(12) United States Patent
Sun et al.

(10) Patent No.: US 10,470,888 B2
(45) Date of Patent: Nov. 12, 2019

(54) INSERT UNIT FOR ARTIFICIAL KNEE JOINT

(71) Applicant: CORENTEC CO., LTD., Cheonan-si, Chungcheongnam-do (KR)

(72) Inventors: Doo-Hun Sun, Seoul (KR); Goon-Hee Lee, Seoul (KR); Oui-Sik Yoo, Seoul (KR); Jung-Woo Seo, Seoul (KR); Yeo-Kyung Kang, Seoul (KR)

(73) Assignee: Corentec Co., Ltd., Cheonan-si, Chungcheongnam-Do (KR)

( * ) Notice: Subject to any disclaimer, the term of this patent is extended or adjusted under 35 U.S.C. 154(b) by 0 days.

(21) Appl. No.: 15/555,044

(22) PCT Filed: Jan. 27, 2016

(86) PCT No.: PCT/KR2016/000877
§ 371 (c)(1),
(2) Date: Aug. 31, 2017

(87) PCT Pub. No.: WO2016/140438
PCT Pub. Date: Sep. 9, 2016

(65) Prior Publication Data
US 2018/0049880 A1    Feb. 22, 2018

(30) Foreign Application Priority Data

Mar. 5, 2015    (KR) .................. 10-2015-0030747

(51) Int. Cl.
*A61F 2/38*    (2006.01)
*A61F 2/46*    (2006.01)
*A61F 2/30*    (2006.01)

(52) U.S. Cl.
CPC .......... *A61F 2/3868* (2013.01); *A61F 2/3886* (2013.01); *A61F 2/46* (2013.01); *A61F 2002/30329* (2013.01)

(58) Field of Classification Search
CPC ........ A61F 2/38; A61F 2/3836; A61F 2/3845; A61F 2/3886
(Continued)

(56) References Cited

U.S. PATENT DOCUMENTS 4,257,129 A * 3/1981 Volz .................. A61F 2/389
623/20.33
5,007,933 A * 4/1991 Sidebotham .......... A61F 2/3886
623/20.27
(Continued)

FOREIGN PATENT DOCUMENTS

EP    0381352 B1    6/1994

OTHER PUBLICATIONS

International Search Report and Written Opinion dated Jun. 22, 2016, issued in PCT Application No. PCT/KR2016/000877, filed Jan. 27, 2016.

*Primary Examiner* — Bruce E Snow
(74) *Attorney, Agent, or Firm* — Workman Nydegger (57) ABSTRACT

The present invention relates to an insert unit inserted during an artificial knee joint operation. An insert unit for an artificial knee joint according to an embodiment of the present invention includes a tibial member configured for coupling to the end of the tibia during an artificial knee joint operation, an insert configured for coupling to an upper side of the tibial member, and a locking rod coupling together the tibial member and the insert by penetrating through the tibial member and the insert, wherein the locking rod comprises a head portion formed at the upper end, and the head portion comprises a lip protruding outward to provide a constraint in relation to the insert during an articular movement such that the locking rod does not dig into the tibial member, to increase a coupling strength of the insert unit.

9 Claims, 11 Drawing Sheets

(58) Field of Classification Search
USPC .................................................. 623/20.27
See application file for complete search history.

(56) References Cited

U.S. PATENT DOCUMENTS

| | | | |
|---|---|---|---|
| 6,080,195 A | 6/2000 | Colleran et al. | |
| 6,165,223 A | 12/2000 | Metzger | |
| 8,137,407 B2 | 3/2012 | Todd | |
| RE44,476 E * | 9/2013 | Meyers | A61F 2/3868 623/18.11 |
| 10,064,733 B2 * | 9/2018 | Metzger | A61F 2/3836 |
| 2004/0225368 A1 | 11/2004 | Plumet | |

* cited by examiner

INSERT UNIT FOR ARTIFICIAL KNEE JOINT

TECHNICAL FIELD

The present invention relates to an insert unit inserted during an artificial knee joint operation and, more particularly, to an insert unit for an artificial knee joint that includes a tibial member coupled to the end of the tibia, an insert coupled to an upper side of the tibial member, and a locking rod that penetrates through and couples together the tibial member and the insert to increase the coupling strength, wherein the locking rod includes a head portion formed on the upper end, a body portion extending from a lower end of the head portion, and an assembly portion recessed into the upper side of the locking rod, the head portion including a lip protruding outward to serve as a detent when inserted into the insert so that the locking rod does not dig into the tibial member, the body portion including a protrusion formed on the outer perimeter to increase the coupling strength of the insert and locking rod, and the assembly portion including an assembly cavity for mating with an inserted device at the upper end of the locking rod, for easier assembly and separation of the locking rod.

BACKGROUND ART

Among the many joints of the human body, the knee joint is the joint that connects the tibia with the femur. There are increasing number of patients whose knee joint has become irrecoverable due to abrasion of the knee joint, aging of the bone tissues, and accidents. The knee joint, which refers to the joint at the knee, is a joint located between the lower end of the femur and upper end of the tibia and the rear side of the patella (knee bone) and enables the leg to bend backwards at the knee.

The symptoms of most diseases in the patella may occur without a particular external wound and may result from a structural or functional anomaly of the patella-femur joint. If the leg is abnormally bent outwards or if the foot is severely outwardly crooked, an excessive force may be applied repeatedly on the patella-femur joint to cause osteomalacia of the articular cartilage. Disuse of the knee joint for extended periods may also cause problems, due to the atrophy and contracture of the quadriceps femoris muscle. If there is a structural anomaly in the patella-femur joint, an assister device may be worn to stabilize the patella, and if there is extensive damage, a surgical procedure of replacing the knee joint with an artificial knee joint may be considered.

Thus, in recent times, operations for surgically replacing irrevocably damaged joints with artificial knee joints have become widespread. In such an operation, an artificial knee joint is generally divided into the femoral member, which is coupled to the end of the femur, the tibial member, which is coupled to the end of the tibia, and the insert, which is positioned between the femoral member and the tibial member. The insert is coupled to an upper side of the tibial member, enabling the femoral member located above to perform a curving or rotating motion at the upper part of the insert.

Figure 1:
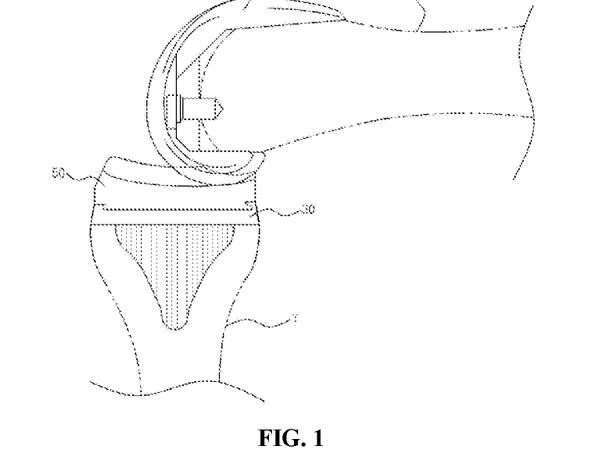
FIG. 1 is a diagram illustrating the coupling and operational relationships between the tibial member, insert, and femoral member.

FIG. 1 is a diagram illustrating the coupling and operational relationships between the tibial member, insert, and femoral member.

Referring to FIG. 1, an artificial knee joint is generally composed of a femoral member 10 coupled to the end of the femur F, a tibial member 30 coupled to the end of the tibia T, and an insert 50 positioned between the femoral member 10 and tibial member 30. The femoral member 10 couples to the end of the femur F to form an articular surface at the end of the femur F, the tibial member 30 couples to the end of the tibia T to form an articular surface at the end of the tibia T, and the insert 50 couples to the upper side of the tibial member 30 to be located between the tibial member 30 and the femoral member 10 and thereby allow the femoral member 10 to slide on the upper surface of the insert 50 to perform a curving or rotating motion and thus enable an articular movement by the artificial joint similar to that of an actual knee joint.

Figure 2:
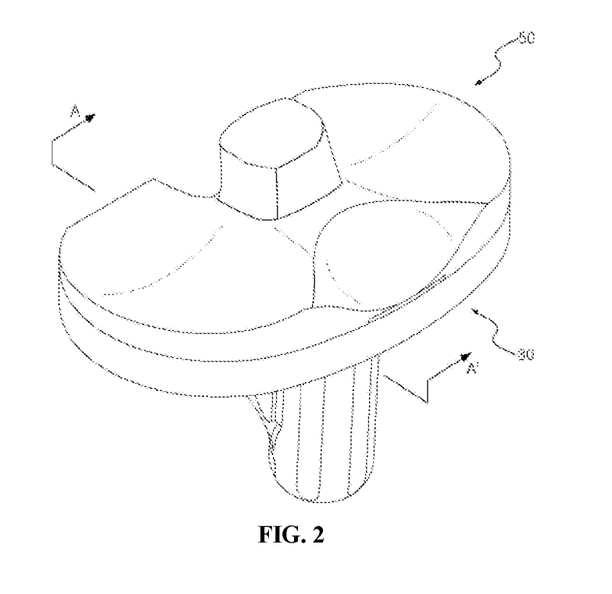
FIG. 2 is a perspective view of an insert unit for an artificial knee joint according to the related art.
Figure 3:
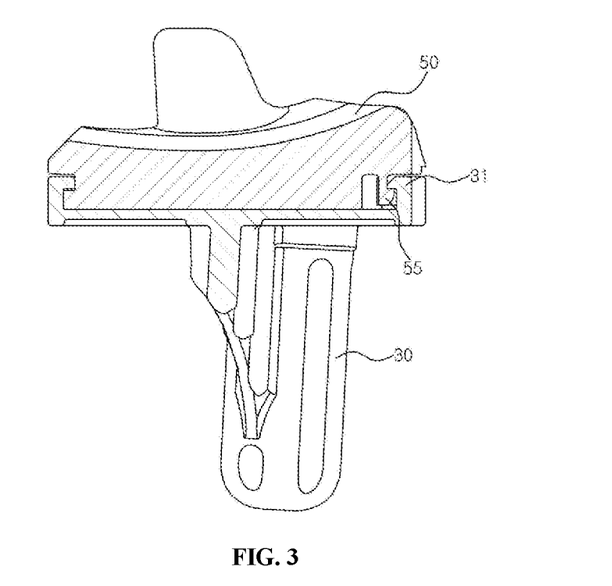
FIG. 3 is a cross-sectional view across line A-A' of FIG. 2.

FIG. 2 is a perspective view of an insert unit for an artificial knee joint according to the related art, and FIG. 3 is a cross-sectional view across line A-A' of FIG. 2.

Referring to FIGS. 2 and 3, the tibial member and the insert 50 are joined by an insert coupling portion 31 and coupler portion 55. However, with an existing insert and tibial member, the actions of bending and unbending the knee and the moment applied by rotations are concentrated on the insert coupling portion 31 and the coupler portion 55, so that there the problem occurs of the tibial member 30 and insert 50 becoming separated, etc.

Thus, there is the need for an insert of a novel structure that can improve the problems of the existing insert.

DOCUMENTS OF RELATED ART (Patent Document 1) Korean Registered Patent No. 10-1352066 (published Jan. 9, 2014) "INSERT FOR ARTIFICIAL KNEE JOINT"

DISCLOSURE

Technical Problem

The present invention has been made keeping in mind the above problems occurring in the related art.

An objective of the present invention is to provide an insert unit for an artificial knee joint operation, the insert unit including a tibial member coupled to the end of the tibia, an insert coupled to the upper side of the tibial member, and a locking rod that penetrates through and couples together the tibial member and the insert, wherein the locking rod includes a head portion formed at the upper end, and the head portion includes a lip that protrudes outwards to provide a constraint in relation to the insert during an articular movement such that the locking rod does not dig into the tibial member, whereby the coupling strength of the insert unit may be increased.

Another objective of the present invention is to provide an insert unit in which the locking rod includes a body portion extending along a vertical direction, and the body portion includes a protrusion protruding from the outer perimeter to increase the coupling strength of the insert unit.

Yet another objective of the present invention is to provide an insert unit in which the protrusion includes an increased-diameter surface that protrudes with an increased diameter from the outer perimeter of the body portion and a sloped surface that decreases in diameter towards a downward direction and forms a slope, to increase the coupling strength of the insert unit.

Still another objective of the present invention is to provide an insert unit in which the body portion includes one or more protrusions to maximize the coupling strength of the insert unit.

Another objective of the present invention is to provide an insert unit in which the locking rod includes an assembly portion at its upper end, wherein the assembly portion includes an assembly cavity for mating with an inserted device in the inner perimeter, to enable easy coupling of the insert unit.

Another objective of the present invention is to provide an insert unit in which the assembly cavity includes a female thread therein for mating with the inserted device to enable easy coupling and separation of the insert unit.

Technical Solution

To achieve the objectives of the present invention above, an insert unit for an artificial knee joint includes the following features.

An insert unit for an artificial knee joint according to an embodiment of the present invention includes a tibial member configured for coupling to the end of the tibia during an artificial knee joint operation, an insert configured for coupling to an upper side of the tibial member, and a locking rod coupling together the tibial member and the insert by penetrating through the tibial member and the insert, wherein the locking rod comprises a head portion formed at the upper end, and the head portion comprises a lip protruding outward to provide a constraint in relation to the insert during an articular movement such that the locking rod does not dig into the tibial member, to increase a coupling strength of the insert unit.

In an insert unit according to another embodiment of the present invention, the insert comprises a mount hole configured to receive the lip placed thereon after the locking rod is inserted.

In an insert unit according to yet another embodiment of the present invention, the insert further comprises a through hole that connects with the lower end of the mount hole and extends downward from the mount hole with a decreasing diameter.

An insert unit according to another embodiment of the present invention includes a tibial member configured to be coupled to the end of the tibia during an artificial knee joint operation, an insert configured for coupling to an upper side of the tibial member, and a locking rod coupling together the tibial member and the insert by penetrating through the tibial member and the insert, wherein the locking rod comprises a body portion extending in a vertical direction, and the body portion comprises a protrusion formed protruding from an outer perimeter thereof to increase the coupling strength of the insert unit.

In an insert unit according to yet another embodiment of the present invention, the protrusion comprises an increased-diameter surface and a sloped surface to increase the coupling strength of the insert unit, wherein the increased-diameter surface protrudes with an increased diameter from the outer perimeter of the body portion, and the sloped surface decreases in diameter towards a downward direction to form a slope.

In an insert unit according to still another embodiment of the present invention, the body portion includes one or more of the protrusions.

An insert unit according to yet another embodiment of the present invention includes a tibial member configured for coupling to the end of the tibia during an artificial knee joint operation, an insert configured for coupling to an upper side of the tibial member, and a locking rod coupling together the tibial member and the insert by penetrating through the tibial member and the insert, wherein the locking rod comprises an assembly portion formed at the upper end, and the assembly portion comprises an assembly cavity in its inner perimeter, with the assembly cavity configured to mate with an inserted device, to enable an easy coupling of the insert unit.

In an insert unit according to still another embodiment of the present invention, the assembly cavity has a female thread formed therein, the female thread configured to mate with the inserted device, to allow easy coupling and separation of the insert unit.

Advantageous Effects

From the embodiments described above and the elements and their coupling and operational relationships described below, the present invention may provide the following advantageous effects.

An embodiment of the present invention includes a tibial member that is coupled to the end of the tibia during an artificial knee joint operation, an insert that is coupled to the upper side of the tibial member, and a locking rod that penetrates through and couples together the tibial member and the insert, wherein the locking rod includes a head portion formed at the upper end, and the head portion includes a lip that protrudes outwards to provide a constraint in relation to the insert during an articular movement such that the locking rod does not dig into the tibial member, whereby the coupling strength of the insert unit may be increased.

In an embodiment of the present invention, the locking rod includes a body portion extending along a vertical direction, and the body portion includes a protrusion protruding from the outer perimeter, so that the coupling strength of the insert unit may be increased.

In an embodiment of the present invention, the protrusion includes an increased-diameter surface that protrudes with an increased diameter from the outer perimeter of the body portion and a sloped surface that decreases in diameter towards a downward direction and forms a slope, so that the coupling strength of the insert unit may be increased.

In an embodiment of the present invention, the body portion includes one or more protrusions to maximize the coupling strength of the insert unit.

In an embodiment of the present invention, the locking rod includes an assembly portion having the locking rod formed at its upper end, and the assembly portion includes an assembly cavity for mating with an inserted device in the inner perimeter, so that the insert unit may be coupled easily.

In an embodiment of the present invention, the assembly cavity includes a female thread therein for mating with the inserted device, so that the insert unit may be coupled and separated easily.

BEST MODE

An insert unit for an artificial knee joint based on the present invention will be described below in more detail with reference to the accompanying drawings. All terms used herein have the same meanings as generally understood by the person having ordinary skill in the field of art to which the present invention pertains unless defined otherwise, and in cases where the generally understood meaning conflicts with the meaning of a term used herein, the definition presented in the specification should be used. In describing the present invention, detailed explanations on certain known functions or elements have been omitted for cases in which it is deemed that such explanations may unnecessarily obscure the essence of the present invention.

Figure 4:
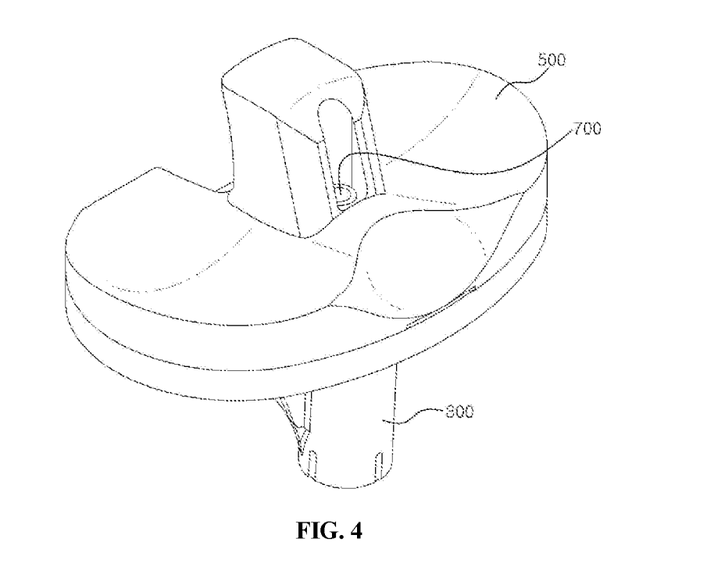
FIG. 4 is an assembled perspective view of an insert unit for an artificial knee joint according to an embodiment of the present invention.

FIG. 4 is an assembled perspective view of an insert unit for an artificial knee joint according to an embodiment of the present invention.

Referring to FIG. 4, an insert unit for an artificial knee joint according to an embodiment of the present invention includes a tibial member 300 that couples to the end of the tibia, an insert 500 that couples to an upper side of the tibial member, and a locking rod 700 that penetrates through and couples together the tibial member and the insert, to increase the coupling strength between the tibial member 300 and the insert 500 and prevent the insert 500 from becoming detached from the tibial member 300.

Figure 5:
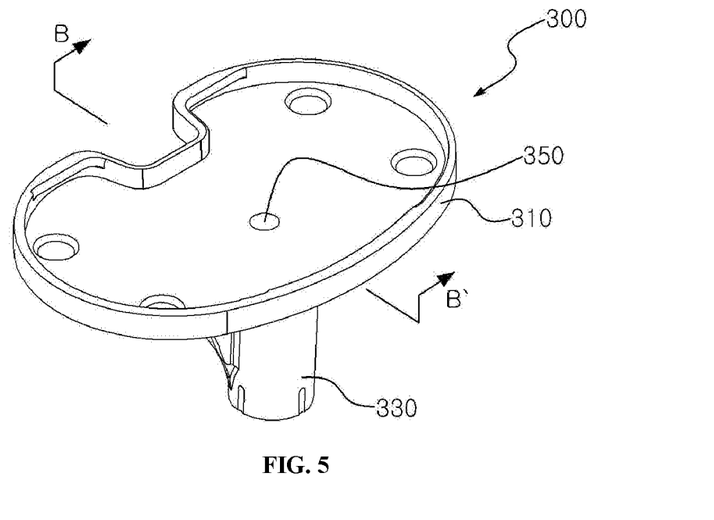
FIG. 5 is a perspective view of the tibial member from FIG. 4.

FIG. 5 is a perspective view of the tibial member from FIG. 4.

Referring to FIG. 5, the tibial member 300 is inserted at the upper side of the tibia, and at the upper side of the tibial member 300 are included an insert coupling portion 310 that couples with the insert 500, a tibia coupling portion 330 that extends downward from a lower side of the upper part to be inserted into the tibia, and a rod coupling hole 350 that is formed in the insert coupling portion 310 in the direction of the tibia coupling portion 330.

The insert coupling portion 310 is positioned at the upper side for coupling the tibial member 300 with the insert 500 and employs coupling by way of protuberances, etc. The insert 500 may be coupled to the insert coupling portion 310 in a variety of ways, such as by a fixed mechanism with which the insert 500 may not move relative to the tibial member 300 or by a movable mechanism with which the insert 500 may move relative to the tibial member 300.

Figure 6:
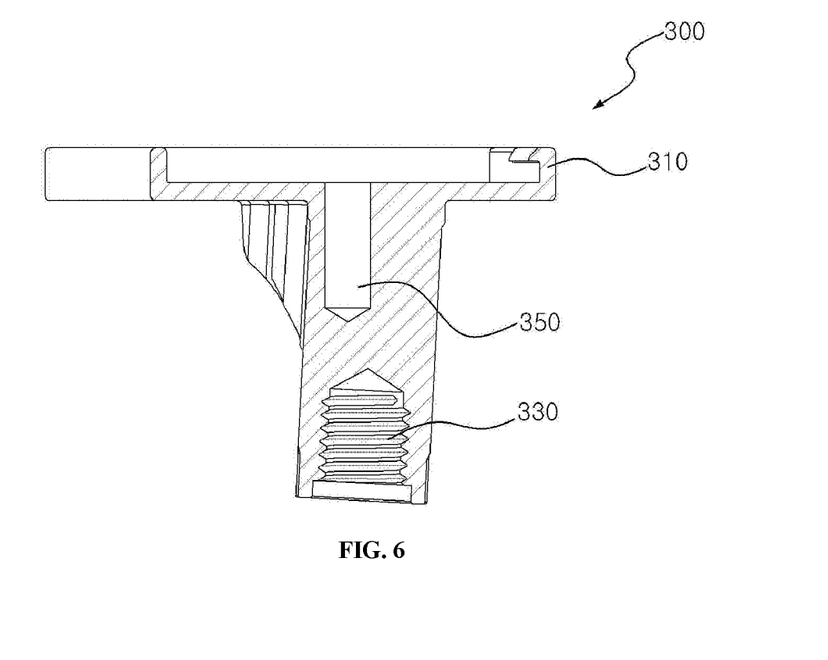
FIG. 6 is a cross-sectional view across line B-B' of FIG. 5.

FIG. 6 is a cross-sectional view across line B-B' of FIG. 5.

Referring to FIG. 6, the tibia coupling portion 330 is an element that is inserted into the tibia and is formed extending downwards from a lower part of the insert coupling portion 310, and a coupling indentation 333 for coupling a tibial stem (not shown) formed at the end, which is inserted into the tibia.

The coupling indentation 333 is formed on the inside for connecting the tibial stem (not shown) that will be inserted into the tibia and may include a female thread, etc.

The rod coupling hole 350 is a cavity formed to connect with the mount hole 531 and through hole 533 of the insert 500 described later on, and the locking rod 700 is pressed into the rod coupling hole, when the locking rod 700 is inserted, so that the coupling between the tibial member 300 and the insert 500 is made more secure.

Figure 7:
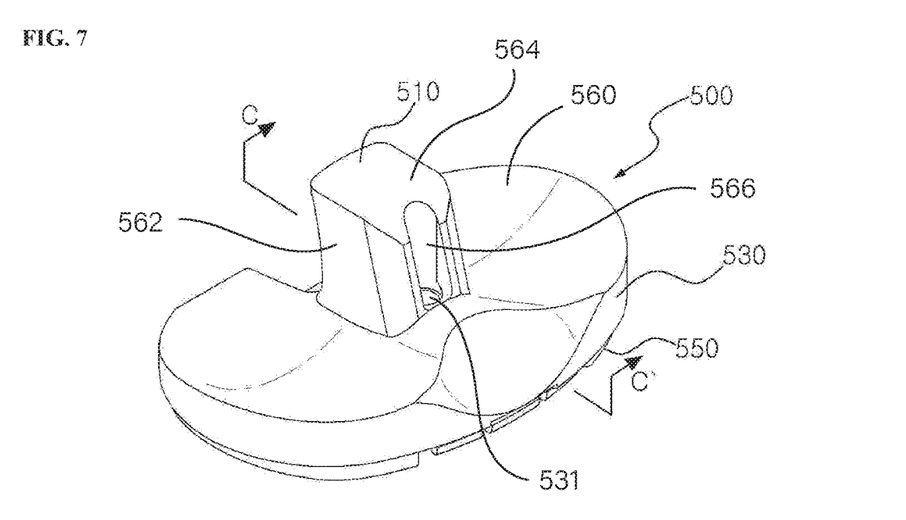
FIG. 7 is a perspective view of the insert from FIG. 4.

FIG. 7 is a perspective view of the insert from FIG. 4.

Referring to FIG. 7, the insert 500 is the element that serves as a substitute for the cartilage of an actual knee joint, is coupled to an upper side of the tibial member 300, and includes a post 510 that protrudes in an upward direction of the insert 500, a connection portion 530 that extends from the lower end of the post 510 and provides an articular surface for enabling an articular movement with the articular surface of the femoral member (not shown), and a coupler portion 550 that is formed at a lower end of the connection portion 530 for coupling with the tibial member 300. Thus, as shown in FIG. 7, connection portion 530 has an upper surface 560 with post 510 protruding outward from upper surface 560. Post 510 has a side surface 562 that terminates at a terminal end face 564.

Figure 8:
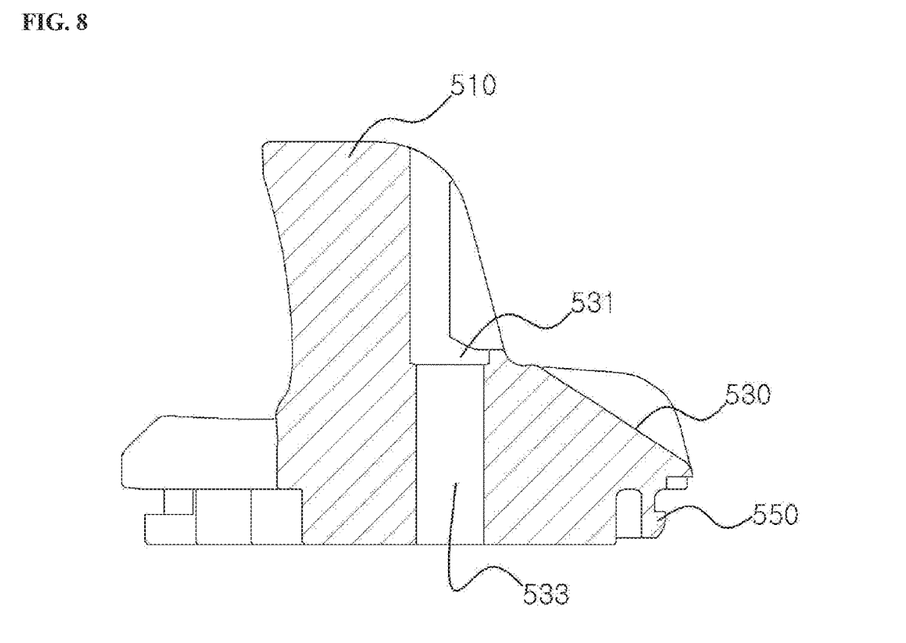
FIG. 8 is a cross-sectional view across line C-C' of FIG. 7.

FIG. 8 is a cross-sectional view across line C-C' of FIG. 7.

Referring to FIG. 8, the post 510 is formed protruding upwards from the insert 500 and guides or controls a movement of the femoral member (not shown) over the insert 500.

The connection portion 530, which is the portion formed at the lower end of the post 510, provides an articular surface that is positioned in both sides, that is, lateral side and medial side, and contacts the articular surface of the femoral member as illustrated in FIG. 1 to enable an articular movement and includes a through hole 533 that connects with the mount hole 531.

The mount hole 531 is recessed to a particular depth, penetrating through a downward direction, at an upper side of the connection portion and receives the head portion 710 of the locking rod 700 described later to provide a more secure coupling between the tibial member 300 and the insert 500. As depicted in FIG. 7, a channel 566 extends through at least a portion of post 510 and is aligned with mount hole 531. At least a portion of channel 566 intersects with side surface 562 of post 510 so that at least a portion of channel 566 is not encircled by post 510. In the depicted embodiment, channel 566 extends through post 510 from terminal end face 564 to upper surface 560 of connection portion 530. FIG. 7 also shows that channel 566 can intersect with side surface 562 of post 510 from terminal end face 564 to upper surface 560 of connection portion 530 so that no portion of channel 566 is completely encircled by post 510.

The through hole 533 is a hole that connects to the lower side of the mount hole 531 and has a decreasing diameter. The locking rod 700, described later on, is inserted and pressed into the through hole 533 so that the insert 500 may be securely coupled to the tibial member 300.

The coupler portion 550 is positioned at the lower side for coupling with the insert coupling portion 310 of the tibial member 300, the coupling being achieved by way of protuberances, etc. The tibial member 300 may be coupled to the coupler portion 550 in a variety of ways, such as by a fixed mechanism with which the tibial member 300 may not move relative to the coupler portion 550 or by a movable mechanism with which the tibial member 300 may move relative to the coupler portion 550.

Figure 9:
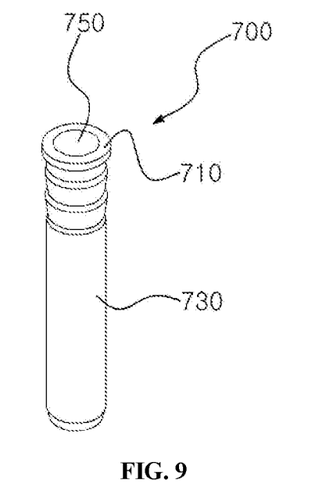
FIG. 9 is a perspective view of a locking rod according to an embodiment of the present invention.

FIG. 9 is a perspective view of a locking rod according to an embodiment of the present invention.

Referring to FIG. 9, the locking rod 700 is the element that is inserted to penetrate through the tibial member 300 and the insert 500. The locking rod 700 reinforces the coupling between the insert coupling portion 310 of the tibial member 300 and the coupler portion 550 of the insert 500 and includes a head portion 710 which protrudes from the upper end of the locking rod 700, a body portion 730 which extends from the lower end of the head portion 710, and an assembly portion 750 which is recessed inward at the upper side of the locking rod 700.

Figure 10:
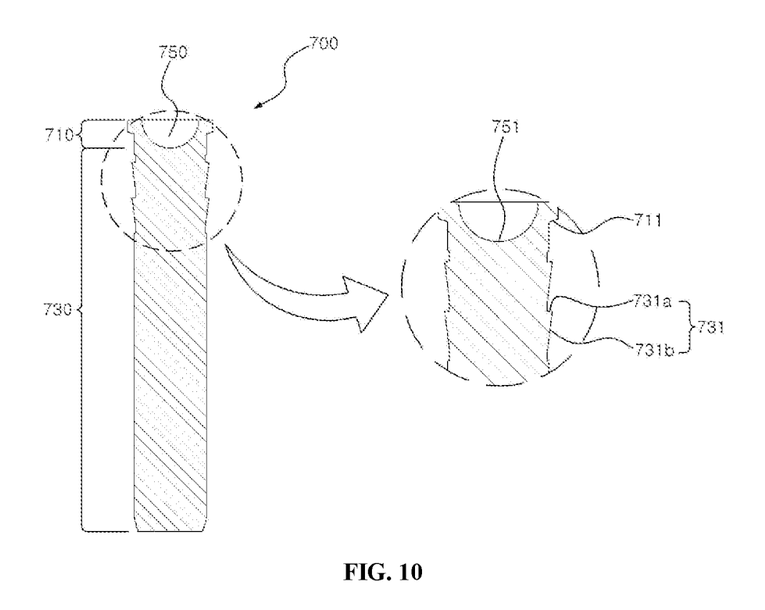
FIG. 10 is a cross-sectional view of the locking rod of FIG. 9.

FIG. 10 is a cross-sectional view of the locking rod of FIG. 9.

Referring to FIG. 10, the head portion 710 is positioned at the upper end of the locking rod 700 and includes a lip 711 that protrudes from the outer perimeter.

The lip 711 protrudes from the outer perimeter of the head portion 710 and prevents digging into the tibial member 300 in cases where an articular movement causes the insert coupling portion 310 of the tibial member 300 to separate from the coupler portion 550 of the insert 500.

The body portion 730 extends from the lower end of the head portion 710 and may include protrusions 731 that protrude from the outer perimeter.

A protrusion 731 is an element that increases the coupling strength with respect to the insert 500, when the locking rod 700 is inserted into the insert 500, and protrudes from an upper side of the body portion 730.

More specifically, a protrusion 731 may include an increased-diameter surface 731*a* that protrudes with an increased diameter from the outer perimeter of the body portion and a sloped surface 731*b* that decreases in diameter towards a downward direction to form a slope, so as to increase the coupling strength by providing a frictional force in the opposite separating direction after insertion. It is possible to form a single protrusion 731, but preferably two or more may be used.

The assembly portion 750 includes an assembly cavity 751 at the upper end of the locking rod 700 for mating with an inserted device.

The assembly cavity 751 is used when inserting the locking rod 700 into the insert 500. When the head portion 710 reaches a particular depth of the mount hole 531, direct insertion of the locking rod 700 becomes difficult whereby the operator requires the use of an assembly device (not shown). The assembly cavity 751 is the cavity with which the assembly device (not shown) engages. Thus, the cross section of the assembly cavity 751 is formed in correspondence to the cross section of the inserted portion of the assembly device (not shown). This may allow for an easier operation and may ensure greater stability and accuracy as the locking rod 700 is pressed into the insert 500.

Figure 11A:
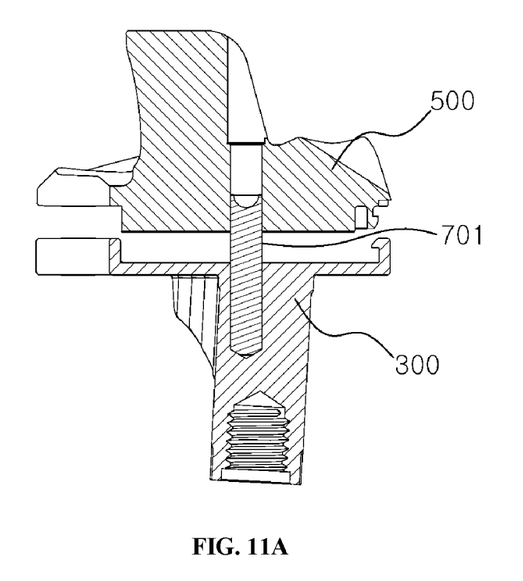
FIGS. 11A and 11B are a diagram illustrating a locking rod that does not include an element corresponding to a lip.
Figure 11B:
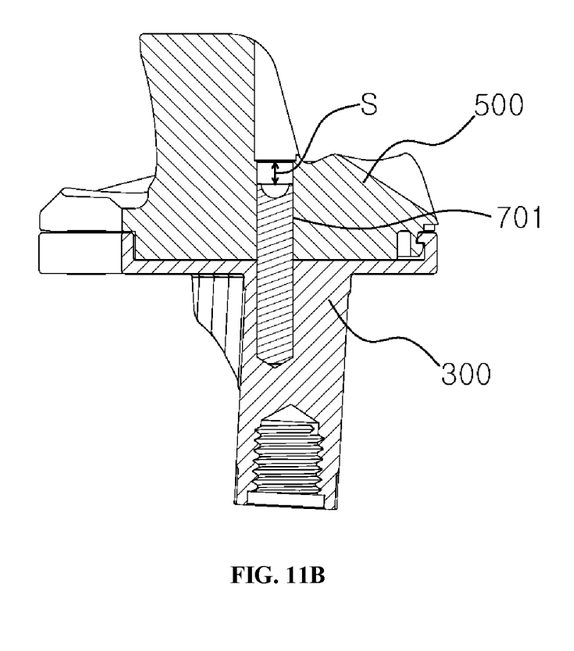

FIGS. 11A and 11B are a diagram illustrating a locking rod that does not include an element corresponding to a lip.

Referring to FIG. 11A, a locking rod 701 that does not include an element corresponding to the lip, if the tibial member 300 and the insert 500 are separated by an articular movement, would remain on the tibial member 300 and dig into the tibial member 300 due to gravity and the articular movement. Referring to FIG. 11B, if the tibial member 300 and the insert 500 are separated by an articular movement and then joined again, a space S would be created in which the locking rod 701 does not touch the insert 500, so that the coupling strength of the insert unit may be weakened.

Figure 12A:
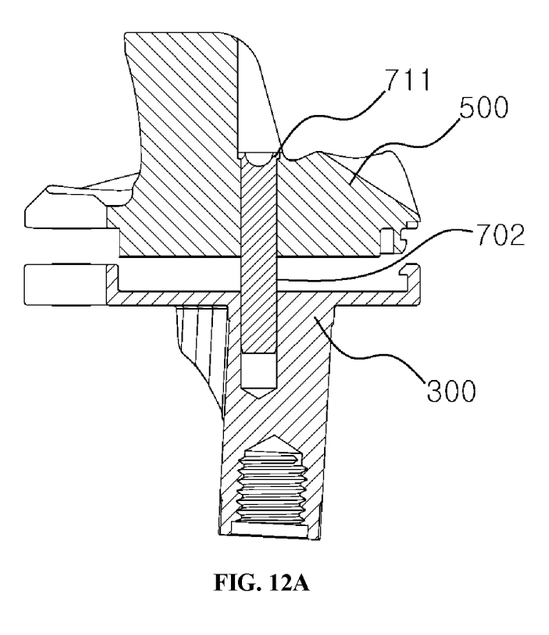
FIGS. 12A and 12B are a diagram illustrating a locking rod that does not include an element corresponding to a protrusion.
Figure 12B:
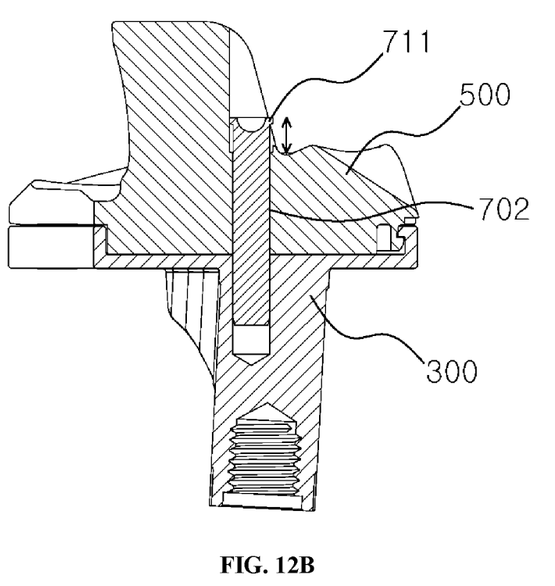

FIGS. 12A and 12B are a diagram illustrating a locking rod that does not include an element corresponding to a protrusion.

Referring to FIG. 12A, a locking rod 702 that does not include an element corresponding to a protrusion, if the tibial member 300 and the insert 500 are separated by an articular movement, would be caught on the insert 500. Referring to FIG. 12B, if the tibial member 300 and the insert 500 are separated by an articular movement and then joined again, the locking rod 702 would not be placed in tight contact with the insert 500, and the locking rod 702 would be vulnerable to movement, so that the coupling strength of the insert unit may be weakened.

Figure 13A:
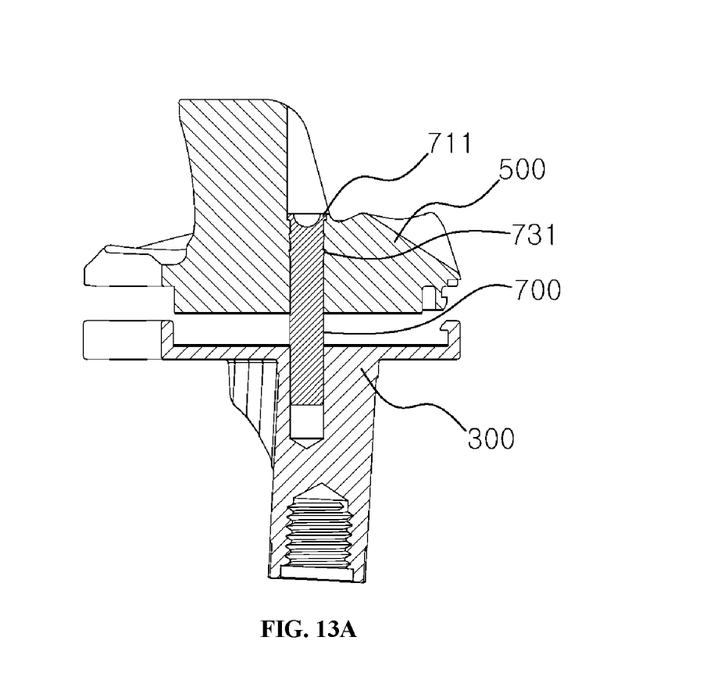
FIGS. 13A and 13B are a diagram illustrating a locking rod according to an embodiment of the present invention that includes elements corresponding to the lip and protrusions.
Figure 13B:
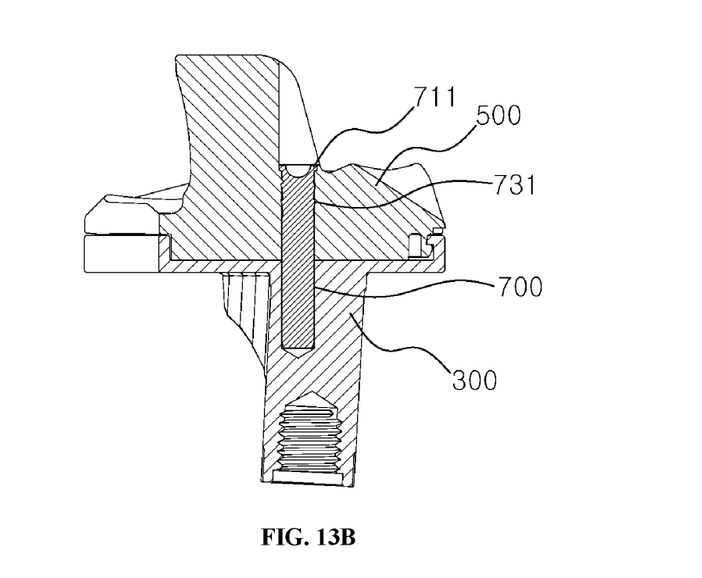

FIGS. 13A and 13B are a diagram illustrating a locking rod according to an embodiment of the present invention that includes elements corresponding to the lip and protrusions.

Referring to FIG. 13A, if the tibial member 300 and the insert 500 are separated due to an articular movement, a locking rod 700 according to an embodiment of the present invention would be caught on the insert 500, and referring to FIG. 13B, if the tibial member 300 and the insert 500 are separated by an articular movement and then joined again afterwards, the locking rod 700 may be placed in tight contact with the insert 500, and the locking rod 700 may not move about, so that the coupling strength of the insert unit may be increased.

Figure 14:
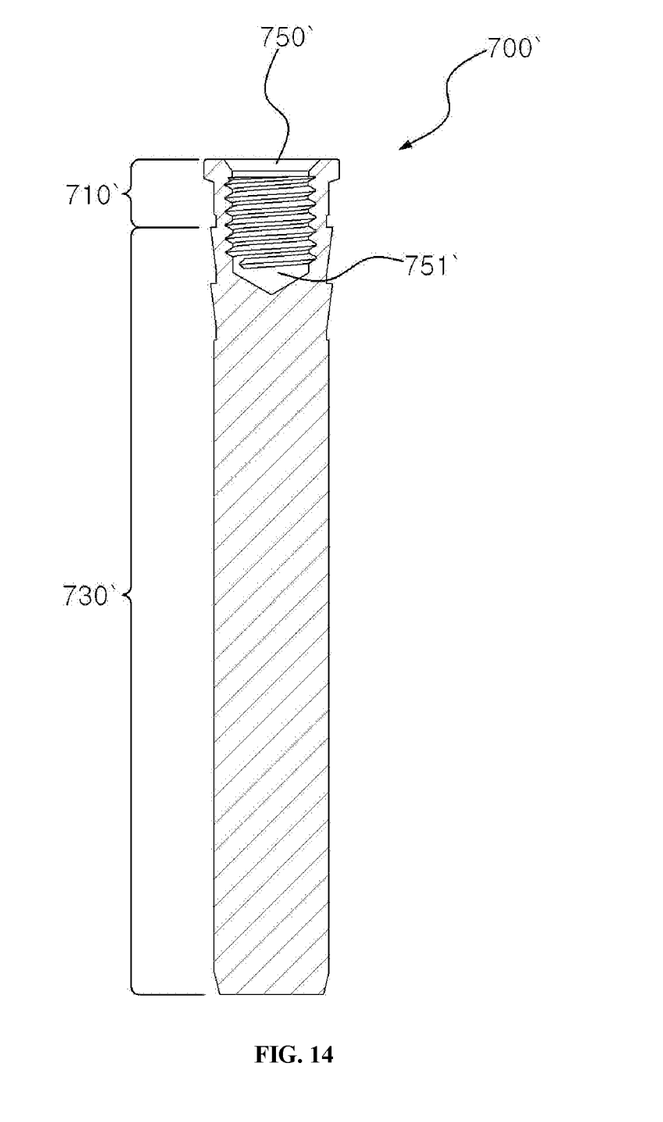
FIG. 14 is a cross-sectional view of a locking rod according to another embodiment of the present invention.

FIG. 14 is a cross-sectional view of a locking rod according to another embodiment of the present invention.

Referring to FIG. 14, the length of the locking rod 700' may be formed differently in different circumstances according to the height of the insert 500, and the locking rod 700' includes an assembly portion 750' formed in a recessed shape at the upper side. Preferably, the assembly cavity 751' of the assembly portion 750' includes a female thread to enable both easier coupling between the locking rod 700' and the insert 500 and easier removal when inserted incorrectly.

Figure 15A:
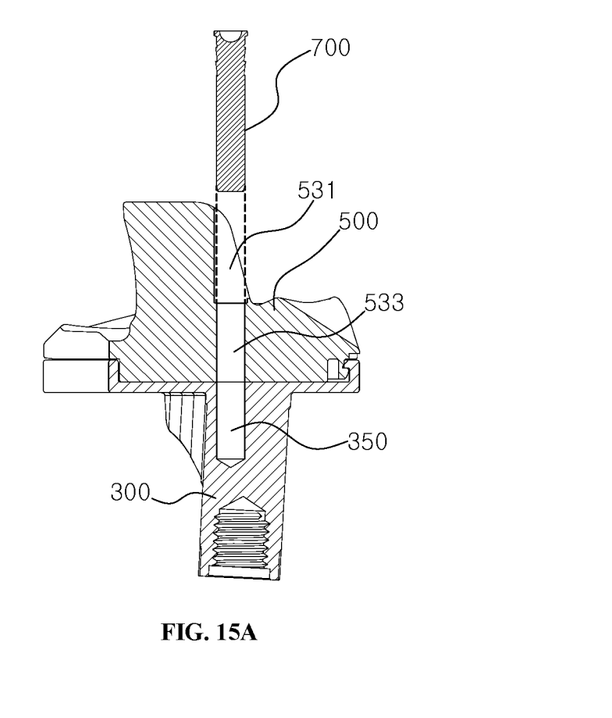
FIG. 15A to 15C are a cross-sectional view illustrating a procedure of inserting the locking rod of FIG. 9 into the insert.
Figure 15B:
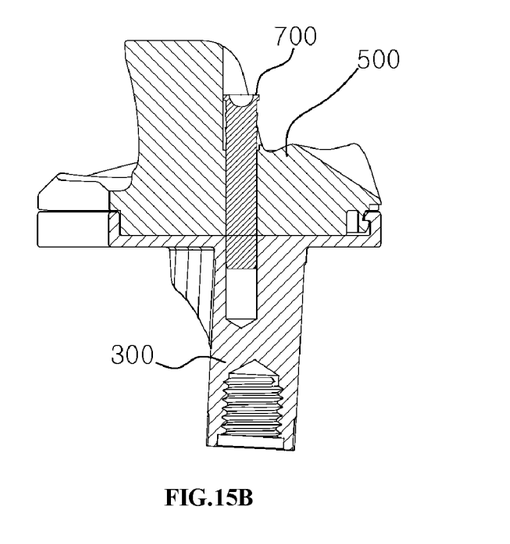
Figure 15C:
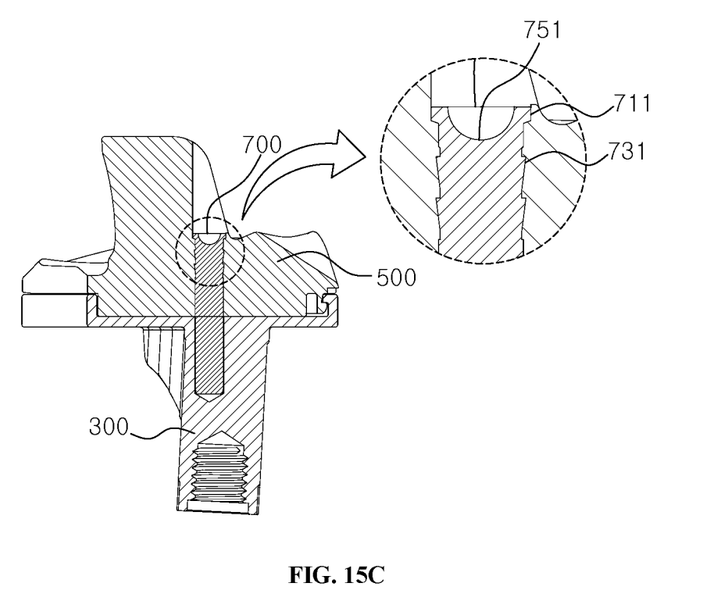

FIG. 15A to 15C are a cross-sectional view illustrating a procedure of inserting the locking rod of FIG. 9 into an insert.

FIG. 15A illustrates a fastening of the tibial member 300 and the insert 500, where the drawing illustrates the situation before the locking rod 700 is inserted. The coupling is achieved using the insert coupling portion 310 of the tibial member 300 and the coupler portion 550 of the insert 500.

Referring to FIGS. 15B and 15C, the locking rod 700 is inserted into the fastened tibial member 300 and insert 500. Until the protrusions 731 are caught on the through hole 533 of the insert 500, the operator inserts the locking rod 700 with the hand. When the protrusions 731 of the locking rod 700 are fit onto the through hole 533, and it becomes difficult for the operator to continue the insertion with the hand, the assembly device (not shown) for engaging the assembly cavity 751 is used to push in the locking rod 700 until the lip 711 of the locking rod 700 is caught on the mount hole 531 of the insert 500. By such procedure, one end of the locking rod 700 is pressed into the insert 500, and the insert 500 and the locking rod 700 are securely coupled.

Also, after the insertion, the protrusions 731 on the body portion 730 of the locking rod 700 provide frictional forces in the opposite, separating direction so that the secure coupling strength is achieved, while the lip 711 allows the head portion 710 of the locking rod 700 to maintain a mounted state on the mount hole 531 of the insert.

Ultimately, once one end of the body portion 730 of the locking rod 700 is inserted into the rod coupling hole 350 of the tibial member 300, the locking rod 700 and the tibial member 300 are secured, after which the protrusions 731 of the locking rod 700 are inserted into the through hole 533 of the insert 500 to apply frictional forces in the opposite direction, i.e. the separating direction, thereby increasing the coupling strength. Thus, a stable coupling strength is provided between the locking rod 700, insert 500, and tibial member 300. In this way, even when a bending moment is applied on the insert 500 after the surgical procedure, the problem of the insert 500 becoming detached from the tibial member 300 is minimized, and the coupling strength of the insert unit is maximized.

While the applicant describes preferred embodiments of the present invention, such embodiments are merely examples of modes in the manner of which the technical spirit of the present invention may be implemented. Any modifications and variations are to be interpreted as lying within the scope of the present invention as long as the technical spirit of the present invention is implemented therein.

The invention claimed is:

1. An insert unit for an artificial knee joint, the insert unit comprising:
    a tibial member configured for coupling to an end of a tibia during an artificial knee joint operation;
    an insert configured for coupling to an upper side of the tibial member, the insert comprising:
        a connection portion having an upper surface;
        a post protruding outward from the upper surface, the post having a side surface that terminates at a terminal end face;
        a mount hole recessed from the upper surface of the connection portion and extending partially into the connection portion, the mount hole having a first diameter;
        a channel extending through at least a portion of the post and being aligned with the mount hole, at least a portion of the channel intersecting with the side surface of the post so that at least a portion of the channel is not encircled by the post;
        a through hole extending downward from the mount hole to a lower surface of the connection portion, the through hole having a second diameter that is less than the first diameter; and
    a locking rod comprising:
        a body extending through the through hole and at least partially into the tibial member to couple the tibial member and the insert together by penetrating through the tibial member and the insert, the body comprising:
            two or more protrusions protruding from an outer perimeter of the body to increase the coupling strength of the insert unit during use, each protrusion comprising an increased-diameter surface and a sloped surface to increase the coupling strength of the insert unit, the increased-diameter surface having a diameter that is greater than a diameter of the body, the sloped surface decreasing in diameter towards a downward direction to form a slope; and
        a head portion formed at an upper end of the body and disposed within the mount hole, the head portion comprising a lip protruding outward and having a third diameter that is larger than the second diameter of the through hole so that the head portion cannot pass through the through hole.

2. The insert unit for an artificial knee joint according to claim 1, wherein at least a portion of the upper surface of the connection portion is an articular surface configured to enable a joint movement with a joint surface of a femoral member.

3. The insert unit for an artificial knee joint according to claim 2, wherein the locking rod is inserted between a lateral side and a medial side of the articular surface of the connection portion.

4. The insert unit for an artificial knee joint according to claim 1, wherein the post is configured to guide or control a movement of the femoral member.

5. The insert unit for an artificial knee joint according to claim 1, wherein the locking rod further comprises an assembly portion formed at an upper end thereof, and the assembly portion comprising an assembly cavity recessed into the locking rod, the assembly cavity configured to mate with an inserted device to enable an easy coupling of the insert unit.

6. The insert unit for an artificial knee joint according to claim 5, wherein the assembly cavity has a female thread formed therein, the female thread configured to mate with the inserted device, to allow easy coupling and separation of the insert unit.

7. The insert unit for an artificial knee joint according to claim 1, wherein third diameter of the lip is greater than the diameter of the increased-diameter surface of the protrusion.

8. The insert unit for an artificial knee joint according to claim 1, wherein the channel extends through the post from the terminal end face to the upper surface of the connection portion.

9. The insert unit for an artificial knee joint according to claim 8, wherein the channel intersects with the side surface of the post from the terminal end face to the upper surface of the connection portion so that no portion of the channel is completely encircled by the post.

* * * * *